United States Patent [19]

Weins et al.

[11] Patent Number: 4,549,437

[45] Date of Patent: Oct. 29, 1985

[54] ACOUSTIC TESTING OF COMPLEX MULTIPLE SEGMENT STRUCTURES

[76] Inventors: Janine J. Weins; Michael J. Weins, both of 6 Allen St., Lebanon, N.H. 03766

[21] Appl. No.: 536,375

[22] Filed: Sep. 27, 1983

[51] Int. Cl.[4] ............................................. G01N 29/04
[52] U.S. Cl. ......................................... 73/587; 73/594
[58] Field of Search ................. 73/587, 594, 572, 801, 73/582, 583, 588

[56] References Cited

U.S. PATENT DOCUMENTS

| | | | |
|---|---|---|---|
| 3,564,903 | 2/1971 | Woodmansee et al. | 73/588 |
| 3,858,439 | 1/1975 | Nakamura | 73/587 |
| 4,006,625 | 2/1977 | Davis | 73/801 |
| 4,128,011 | 12/1978 | Savage | 73/632 |

Primary Examiner—Anthony V. Ciarlante

[57] ABSTRACT

The present invention relates to a method for acoustic testing of multiple segment complex structures for detecting changes in the integrity of such structures to anticipate failure. The method of the present invention in its simplest form requires providing each segment of a complex multiple segment structure with at least one acoustic sensor, recording the intensity and frequency distribution of the acoustic waves sensed by such acoustic sensor; and finally comparing the acoustic waves that are sensed either against a standard, over time, and/or from one segment of the complex multiple segment structure to another segment of the complex multiple segment structure.

11 Claims, 4 Drawing Figures

ACOUSTIC TESTING OF COMPLEX MULTIPLE SEGMENT STRUCTURES

DESCRIPTION

1. Field of Invention

The present invention relates to acoustic testing of complex multiple segment structures for the purpose of detecting time dependent and/or structure dependent changes in the integrity of such structures.

2. Background Art

Each year many complex multiple segment mechanical structures fail. These failures can cause economic loss, schedule delays and may even cause death as was the case in June of 1983 when a portion of a bridge which carried Interstate 95 traffic failed.

In an effort to avoid the failure of complex multiple segment structures the structures are initially designed with generous safety factors; during use and/or exposure to deteriorating environmental conditions the complex multiple segment structures are frequently inspected and tested; and/or the complex multiple segment structures are replaced at intervals deemed to be sufficiently often to assure that the structures will not fail in service. In spite of the current precautions taken to assure that failure of complex multiple segment structures will not occur, some do fail. Additional precautions can and should be taken to further reduce the occurrence of such failures.

It is an object of the present invention to provide a method for anticipating the impending failure of a complex multiple segment structure.

An object of the present invention is to provide a method for monitoring the structural integrity of complex multiple segment structures that will supplement existing visual inspection procedures and thereby reduce the incidence of unanticipated catastrophic failures.

Another object of the present invention is to provide a method for identifying which of a series of complex multiple segment structures is most likely to fail in a catastrophic and/or premature manner.

These and other objects of the present invention will become apparent from the following description, figures and claims.

SUMMARY OF INVENTION

The present invention relates to a method of testing, monitoring and inspecting complex multiple segment structures, and in particular the method of the present invention relates to acoustic testing of such complex multiple segment structures to predict the structural integrity of such structure by either identifying differences in the acoustic emissions of different segments of similar construction, or by determining changes as a function of time and/or usage in the complex multiple segment structures.

The method of the present invention in its simplest form requires providing each segment of a complex multiple segment structure with at least one acoustic sensor, recording the intensity and frequency distribution of the acoustic waves sensed by such acoustic sensor; and finally comparing the acoustic waves that are sensed either against a standard, or over time and/or from one segment of the complex multiple segment structure to another segment of the complex multiple segment structure.

BEST MODES FOR CARRYING THE INVENTION INTO PRACTICE

The methods of the present invention can be used to inspect, monitor and test any of a variety of complex multiple segment structures including but not limited to bridges, airplanes, storage tanks and/or crane booms.

The present invention relates to a method of testing and inspecting complex multiple segment structures, and in particular the method of the present invention relates to acoustic testing of such complex multiple segment structures to determine structural integrity; changes in structural integrity from one segment of the complex multiple segment structure to another segment of the complex multiple segment structure; and/or deterioration as a function of time and usage of such complex multiple segment structures.

The method of the present invention in its simplest form requires providing each segment of a complex multiple segment structure with at least one acoustic sensor, recording the intensity and frequency distribution of the acoustic wave sensed by the acoustic sensor, and finally comparing the acoustic waves that are sensed against a standard, over time, and/or from one segment of the complex multiple segment structure to another segment of the complex multiple segment structure.

Figure 1:
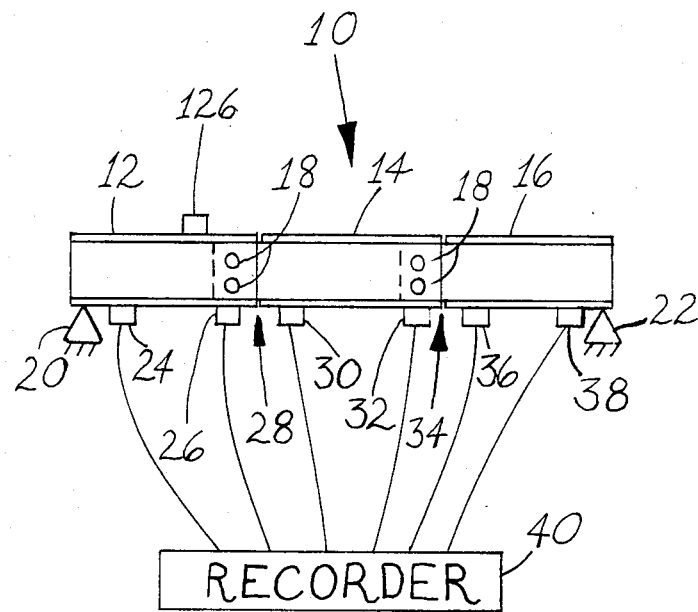
FIG. 1 is a schematic representation of a monitoring configuration for recording the acoustic emissions of a multiple segment structure in accordance with the teachings of the present invention.

FIG. 1 is a schematic representation of an acoustic monitoring and recording system. The multiple segment structure 1 shown in FIG. 1 has three segments 12, 14 and 16 of similar construction. These segments are rigidly connected by fastening means 18 such as rivets or bolts. The structure is supported by a first support 20 and a second support 22. The acoustic emission from each of the segments is detected by acoustic sensors, such as piezoelectric transducers, which convert the acoustic emission into electric potentials. The electric potentials may be recorded and/or processed. In FIG. 1 two transducers are attached to each segment. The first segment 12 has a first transducer 24 positioned in close proximity to the first support 20 and a second transducer 26 positioned near the first junction 28 of the first segment 12 and the second segment 14.

A third transducer 30 is located on the second segment 14 near the first junction 28 while a forth transducer 32 is positioned on the second segment 14 near the second junction 34 where the second segment 14 joins the third segment 16.

A fifth transducer 36 is positioned on the third segment 16 near the second junction 34 while a sixth transducer 38 is positioned on the third segment 16 near the second support 22.

Each of the transducers are electrically connected to a multiple channel recorder 40. The multiple channel recorder 40 records the acoustic emissions from each of the transducers.

Figure 2:
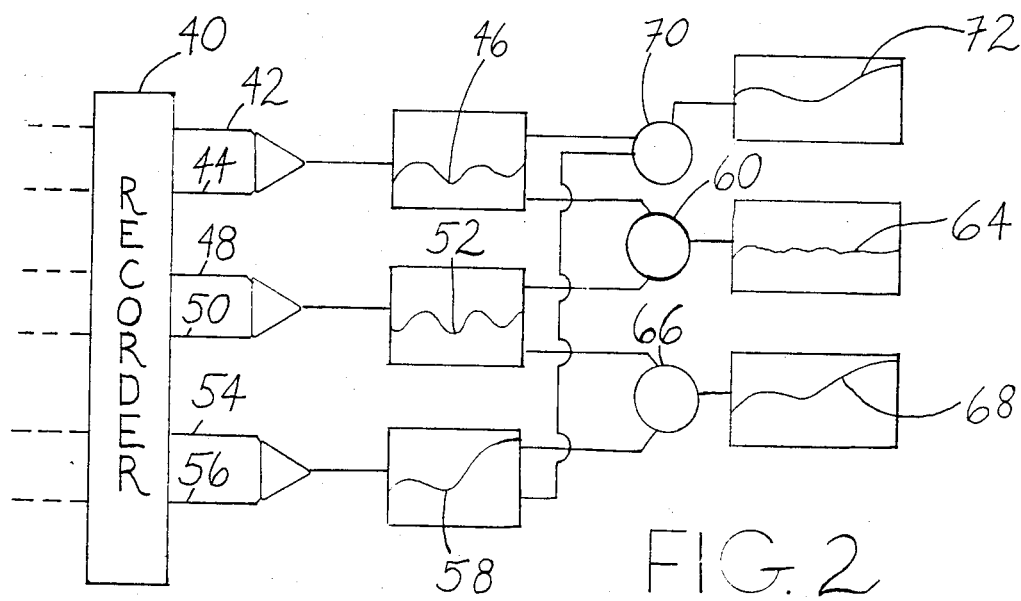
FIG. 2 is a schematic representation of a system for analyzing a broad spectrum of acoustic emissions, white noise, in accordance with the present invention. The white noise is sensed by acoustic sensors such as shown in FIG. 1. The acoustic emissions are then fed to an analyzing system such as shown in FIG. 2 where the acoustic emissions are summed for each of the segments of the structure. Finally the summed acoustic emissions are compared.

FIG. 2 is a schematic representation of a system for analyzing broad spectrum acoustic emissions, white noise, in accordance with the present invention. The white noise is sensed by sensors positioned in a manner such as depicted in FIG. 1. The acoustic emissions generated at each of the sensors can be fed to the system shown in FIG. 2 where the generated signals are summed for each segment of the structure.

The output signal 42 of the recorder 40, which is the recorded signal from the first transducer 24, is added to the output signal 44 of the recorder 40 which is the recorded signal from the second transducer 26, to produce a time dependent summed output signal for segment 12. This summed output signal for segment 12 is schematically represented by the signal 46.

In a similar manner the output signals 48 and 50, which are respectively the recorded signals from transducers 30 and 32 located on the second segment 14 of the complex multiple segment structure are summed. Summing signals 48 and 50 provides a summed output signal for segment 14 which is schematically represented by the signal 52.

The same summing procedure is done for the output signals 54 and 56 from the transducers located on the third segment 16 of the complex multiple segment structure. This provides a time dependent summed output signal for the third segment which is schematically represented by 58.

The summed output signals 46, 52 and 58 can be visually compared and differences in the patterns noted. These differences over time will be a result of changes in the structural integrity of the individual segments of the complex multiple segment structure.

The comparison of the output signals can be done automatically by processing pairs of the summed output signals in such a manner that the output signals are subtracted and their difference recorded. For example, signal 46 and 52 can be fed into an analyzer 60 which would then subtract signal 46 from signal 52 to produce a difference output signal 64. In a similar manner summed output signals 52 and 58 can be processed by analyzer 66 to produce a difference signal 68, and finally summed output signals 46 and 58 can be fed to analyzer 70 where they may be subtracted to produce a difference signal 72. The difference signals can be compared over time to determine deterioration in the structural integrity of the complex multiple segment structure.

Testing in accordance with this embodiment of the present invention will provide an integrated acoustic signal that will be most sensitive to global defects such as missing bolts and fractured support members.

Figure 3:
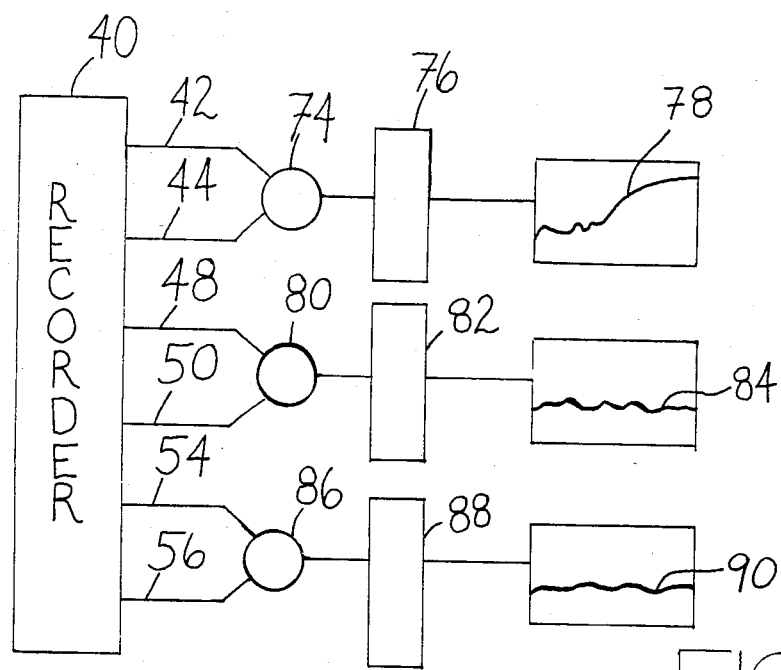
FIG. 3 is a schematic representation of a system for filtering acoustic emissions. The acoustic emissions can be filtered prior to comparison and analysis.

FIG. 3 is a schematic representation of a system for analyzing filtered noise in accordance with a preferred embodiment of the present invention. When the complex multiple segment structure is monitored in accordance with this preferred embodiment the white noise is filtered and the emissions monitored are principally the acoustic emissions associated with the generation of internal defects such as cracks forming within the structure.

With this technique differences in the paired output signals of each segment are analyzed after filtration. For the structure of FIG. 1 the signals 42 and 44 are combined in an analyzer 74 to provide a difference signal which is passed through a filter 76 which eliminates those frequencies below 100 KHz. This filtration would remove the lower frequency acoustic emissions which result from traffic and mechanical interaction of the individual segments. The time dependent output signal represented schematically by 78 may be reviewed. This filtered signal 78 will grow over time if cracks are initiated and grow. The initiation of growth of the output signal over time will indicate that the first stage of failure has occurred.

In a similar manner output signals 48 and 50 can be combined in analyzer 80 and then filtered by a 100 KHz filter 82 to produce a time dependent filtered signal 84. Output signals 54 and 56 can be combined in analyzer 86 and filtered with a 100 KHz filter 88 to produce a filtered output signal 90.

Inspecting a structure in accordance with the embodiment described above and depicted in FIG. 3 will provide information on changes in the internal structure. Changes over time in the acoustic wave generated in accordance with this method will indicate the time dependent change of internal defects such as the dislocation structure. Filtered signal 78 as depicted in FIG. 3 shows a time dependent growth indicating crack initiation and growth in the first segment 12 of the complex multiple segment structure.

Any of the above methods of the present invention can be used to analysis paired output signals. For example if one were interested in inspecting the junction 28 of the complex multiple segment structure 10 shown in FIG. 1 the difference in the output signals of acoustic sensors 26 and 30 could be taken. This output signal could then be analyzed in the manners described above. Likewise the acoustic emissions sensed by acoustic sensor 126 shown in FIG. 1 could be combined with the acoustic emissions sensed by acoustic sensor 26 and this combined acoustic output signal could be analyzed and compared with similar acoustic output signals in the manners described above.

Complex multiple segment structures can be monitored in accordance with yet another embodiment of the present invention by first generating an acoustic wave at one location and sensing the acoustic wave at another location. This method allows one to observe the attenuation of an acoustic wave. A change in the attenuation of an acoustic wave indicates a change in the path of the acoustic wave and therefore indicates a difference in the connectivity of the structure. This change in the connectivity can be the result of the absence, or fracture of an element. For testing in accordance with this embodiment the acoustic wave should be generated and sensed when the structure is not being subject to external forces which could generate additional acoustic waves. Therefore it is preferred when testing a structure such as a bridge in accordance with this embodiment to do so at times when traffic flow is at a minimum.

Figure 4:
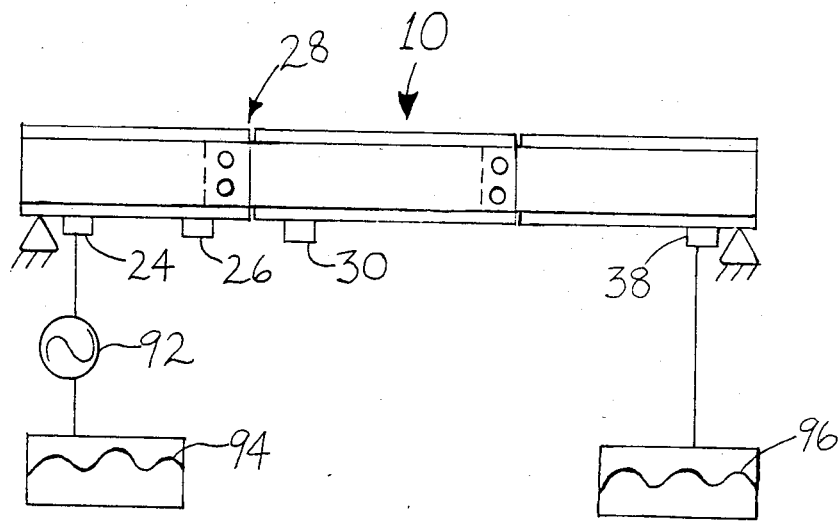
FIG. 4 is a schematic representation of one embodiment of the present invention in which the acoustic emission responsive to a generated signal is recorded and analyzed.

FIG. 4 is a schematic representation of the embodiment of the present invention in which the inspection is carried out by monitoring a generated acoustic signal in the complex multiple segment structure 10 of FIG. 1. In this embodiment the first transducer 24 is driven by a signal generator 92, this causes an acoustic signal 94 to be generated and transmitted to the complex multiple segment structure. The acoustic signal 94 is transmitted through the complex multiple segment structure and sensed by the transducer 38. The difference between the generated signal 94 and the signal 96 sensed by the transducer 38 is a function of the acoustic conductivity of the multiple segment structure 10. Initially the acoustic wave sensed by the sensor 38 can be compared to a standard to determine connectivity of the complex multiple segment structure. If during assembly of such a complex multiple segment structure a connecting pin or other such connecting element is omitted such would be indicated by the inability of the complex multiple segment structure to transmit the higher frequency acoustic waves.

Changes in the structural integrity of the complex multiple segment structure 10 can be detected by periodically generating a standard signal, recording the transmitted signal, and comparing the recorded transmitted signals over time. If changes over time in the transmitted signal are detected the location of the changes can be more closely ascertained by reducing the spacial separation of the signal generating transducer and the acoustic sensors. For example, examination of the first junction 28 could be accomplished by employing the transducer 26 to transmit a generated acoustic wave and the transducer 30 could be used to record the transmitted signal.

What we claim is:

1. An in service method of monitoring the structural integrity of a complex multiple segment structure, such method comprising the steps of:
    (a) providing at least one acoustic sensor to each segment of the complex multiple segment structure;
    (b) recording acoustic emissions sensed by said acoustic sensor, said acoustic emissions resulting from said service; and
    (c) analyzing the time dependence of said recorded acoustic emissions to determine deviations.

2. The method of claim 1 wherein said analysis further comprises the additional step of:
    (d) comparing the acoustic emissions sensed on each segment of the complex multiple segment structure.

3. The method of claim 2 wherein said comparison is done on signals obtained by subtracting the acoustic emissions of each segment of the complex multiple segment structure from the acoustic emissions of another segment of the complex multiple segment structure.

4. The method of claim 2 wherein at least two acoustic sensors are provided for each of said segments, and said acoustic emissions sensed on each segment is the result of the combination of the acoustic emissions sensed by all acoustic sensors on each segment.

5. The method of claim 4 wherein said combination is by addition.

6. The method of claim 2 wherein each segment is provided with an even number of acoustic sensors, and the acoustic signals used for comparison are obtained by subtracting the acoustic emissions of pairs of acoustic sensors.

7. The method of claim 6 wherein said comparison is made by examining the signals obtained by subtracting the acoustic emissions of each segment of the complex multiple segment structure from the acoustic emissions of another segment of the complex multiple segment structure.

8. The method of claim 6 wherein at least two pairs of acoustic sensors are provided for each of said segments, and said acoustic emissions on each segment is the result of the combination of the acoustic emissions sensed by all pairs of acoustic sensors on each segment.

9. The method of claim 8 wherein said combination is by addition.

10. The method of claim 1 wherein the acoustic emissions sensed by said acoustic sensors are filtered prior to analysis.

11. The method of claim 10 wherein the filter used to filter the acoustic emissions is a 100 KHz filter.

* * * * *